(12) United States Patent
Calveras et al.

(10) Patent No.: US 9,719,979 B2
(45) Date of Patent: Aug. 1, 2017

(54) METHODS OF IDENTIFYING CROSSLINKING MOLECULES FOR POLYMERS

(71) Applicant: SABIC Global Technologies B.V., Bergen op Zoom (NL)

(72) Inventors: Jordi Calveras, Evansville, IN (US); Thomas L. Evans, Mount Vernon, IN (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/036,213

(22) PCT Filed: Nov. 14, 2014

(86) PCT No.: PCT/US2014/065736
§ 371 (c)(1),
(2) Date: May 12, 2016

(87) PCT Pub. No.: WO2015/073847
PCT Pub. Date: May 21, 2015

(65) Prior Publication Data
US 2016/0290986 A1    Oct. 6, 2016

Related U.S. Application Data

(60) Provisional application No. 61/904,640, filed on Nov. 15, 2013, provisional application No. 62/014,368, filed on Jun. 19, 2014.

(51) Int. Cl.
*G01N 33/44* (2006.01)
*C08G 64/14* (2006.01)

(52) U.S. Cl.
CPC .......... *G01N 33/442* (2013.01); *C08G 64/14* (2013.01)

(58) Field of Classification Search
CPC ..................................................... G01N 33/44
(Continued)

(56) References Cited

U.S. PATENT DOCUMENTS 4,121,001 A * 10/1978 Gotcher ............... C07C 317/00
                                                                174/110 FC
4,230,548 A * 10/1980 Adelmann ............. C08G 63/64
                                                                522/163
(Continued)

FOREIGN PATENT DOCUMENTS

| EP | 1 369 135 A1 | 12/2003 |
| WO | WO 2010/115884 A1 | 10/2010 |
| WO | WO 2011/143524 A2 | 11/2011 |

OTHER PUBLICATIONS

Bellus, D. et al, Polymer Letters 1966, 4, 1-5.*
(Continued)

*Primary Examiner* — Arlen Soderquist
(74) *Attorney, Agent, or Firm* — Richard M. Klein; Fay Sharpe LLP

(57) ABSTRACT

Methods for screening molecules or moieties for their ability to crosslink are disclosed. An aromatic carbonate, aromatic ester, or aliphatic ester group is attached to the molecule to mimic the presence of a polymer. A solution of the modified molecule is irradiated, and the first-order kinetic rate constant is measured. If the rate constant is high enough or a threshold amount of the molecule is consumed, a polymer is synthesized using the molecule/moiety as an endcap or co-monomer. The polymer is irradiated, and the increase in crosslink density and the gel formation percentage are determined. These parameters, if high enough, indicate the suitability of the molecule/moiety to act as a crosslinking agent, particularly for polycarbonates. Alternatively, the
(Continued)

molecule/moiety may be identified as suitable solely by its first-order kinetic rate constant.

16 Claims, 5 Drawing Sheets

(58) Field of Classification Search
USPC .......................................................... 436/34
See application file for complete search history.

(56) References Cited

U.S. PATENT DOCUMENTS

| | | | | |
|---|---|---|---|---|
| 5,362,838 | A * | 11/1994 | McGrath | C08G 64/045 528/171 |
| 6,043,334 | A * | 3/2000 | Kanamaru | C08G 64/045 430/58.35 |
| 6,151,042 | A * | 11/2000 | Smith | B41J 2/14032 347/20 |
| 2006/0029871 | A1 * | 2/2006 | Hu | G03G 5/051 430/58.7 |
| 2006/0029873 | A1 * | 2/2006 | Bender | C08G 64/10 430/59.6 |
| 2009/0209695 | A1 * | 8/2009 | Yu | C08L 67/02 524/451 |
| 2014/0272691 | A1 * | 9/2014 | Calveras | G03F 7/027 430/18 |
| 2014/0275321 | A1 * | 9/2014 | Morizur | C08G 64/14 522/111 |
| 2014/0275324 | A1 * | 9/2014 | Morizur | C08G 64/14 522/178 |

OTHER PUBLICATIONS

Coppinger, G. M. et al, Journal of Physical Chemistry 70, 3479-3489.*
Bellus, D. et al, Chemical Reviews 1967, 67, 599-609.*
Davis, A. et al, Journal of the Chemical Society B: Physical Organic 1968, 425-427.*
Caress, E. A. et al, Journal of Organic Chemistry 1971, 36, 769-772.*
Caress, E. A. et al, Journal of Organic Chemistry 1972, 37, 3160-3163.*
Humphry, J. S. et al, Macromolecules 1973, 6, 305-314.*
Webb, J. D. et al, Macromolecules 1986, 19, 2810-2825.*
Rivaton, A. et al, European Polymer Journal 2002, 38, 1349-1363.*
Loshaek, S. and Fox, T.G. Cross-linked Polymers. I. Factors Influencing the Efficiency of Cross-linking in Copolymers of Methyl Methacrylate and Glycol Dimethacrylates; Journal of the American Chemical Society; vol. 75; No. 14; pp. 3544-3550; 1953.
International Search Report for PCT/US2014/065736 dated Jan. 23, 2015.

* cited by examiner (Zero Passes)

(Five Passes)

METHODS OF IDENTIFYING CROSSLINKING MOLECULES FOR POLYMERS

BACKGROUND

The present disclosure relates to methods for identifying suitable crosslinking molecules or moieties for polymers. These methods are particularly suitable for identifying crosslinking moieties that can be useful with polycarbonates incorporating aromatic compounds.

Crosslinking of polymeric chains is a common method for modifying polymers because of its influence on mechanical properties, mobility, solubility, and diffusion. Polymers can be crosslinked after synthesis by the addition of a crosslinking agent. Such crosslinking agents may crosslink upon heating or irradiation.

It would be desirable to provide methods of studying and choosing potential crosslinking agents that are suitable for a given polymer and application.

BRIEF DESCRIPTION

Disclosed herein are methods for selecting a suitable crosslinking agent, particularly for polycarbonate polymers. The methods include a quantitative estimation of crosslinking activity and a qualitative assessment of the degree of crosslinking. These provide a fast screening method which can reduce the time needed to identify crosslinking agents that are suitable for a given application.

Disclosed in various embodiments are methods of identifying a suitable crosslinking agent, comprising: synthesizing an aromatic carbonate derivative, aromatic ester derivative, or aliphatic ester derivative of a crosslinker candidate to form an initial product; irradiating a solution containing a known concentration of the initial product for a first time period; and determining whether a first threshold amount of the initial product disappeared during the first time period. If the first threshold amount was exceeded, then the methods further include: determining a first-order kinetic rate constant of the initial product; synthesizing at least one article from a polymer that contains the crosslinker candidate as an endcap; irradiating the at least one article with a specified UV dosage; determining an increase in crosslink density of the article after the irradiation with the specified UV dosage; measuring a gel formation percentage of the article after the irradiation with the specified UV dosage; and based on the first-order kinetic rate constant, the increase in crosslink density, and the gel formation percentage, identifying the crosslinker candidate as a suitable crosslinking agent.

In other embodiments described herein, the first-order kinetic rate constant may be used independently to determine the suitability of a crosslinker candidate, without consideration of the increase in crosslink density or the gel formation percentage.

The solution containing a known concentration of the initial product may include (a) dichloromethane and (b) a linear alkyl alcohol. The volume ratio of dichloromethane to the linear alkyl alcohol may be about 80:20. The linear alkyl alcohol may be methanol or ethanol.

The solution is usually irradiated with ultraviolet light. The first time period may be about 30 minutes. The solution can be irradiated with an ultraviolet light dosage of about 5 $J/cm^2$ to about 90 $J/cm^2$ of UVA radiation.

The at least one article may be irradiated with ultraviolet light.

The crosslinker candidate may be identified as a suitable crosslinking agent if the first-order kinetic rate constant is at least 0.220 $min^{-1}$ in ethanol, the increase in crosslink density is at least 0.0015, and the gel formation percentage is at least 6%.

The methods may further comprise periodically sampling the solution during the first time period to obtain a plurality of samples, and measuring a remaining amount of the initial product in each sample.

The methods may further comprise periodically measuring the crosslink density of the at least one article during the irradiation with the specified UV dosage.

The increase in crosslink density x may be determined by a formula described further herein. The gel formation percentage can be measured by weighing the article; dissolving the article in dichloromethane to obtain the gel; and weighing the gel to obtain the ratio of gel weight to article weight.

In specific embodiments, the aromatic carbonate derivative is the phenyl carbonate derivative of the crosslinker candidate. The aromatic carbonate derivative of the crosslinker candidate can be synthesized by reacting the crosslinker candidate with phenyl chloroformate In other embodiments, the aromatic ester derivative is a phenyl ester derivative of the crosslinker candidate, or the aliphatic ester derivative is a linear alkyl ester derivative of the crosslinker candidate. Each can be synthesized by reacting the crosslinker candidate with a phenyl or alkyl alcohol, respectively, and a catalytic amount of acid.

Alternatively, suitable crosslinking agents, both monomer candidates and endcapping candidates, may also be selected based solely on the first-order kinetic rate constant for the disappearance of initial product during the first time period. The crosslinker candidate may be identified as a suitable crosslinking agent if the first-order kinetic rate constant is at least 0.12 $min^{-1}$ in ethanol if the candidate is a potential crosslinking endcap, or at least 0.04 $min^{-1}$ in ethanol if the candidate is a potential crosslinking monomer.

Also disclosed herein are methods for selecting an aromatic ketone endcapping agent for a crosslinkable polycarbonate, comprising: synthesizing a model compound containing (i) an aromatic ketone containing moiety and (ii) either a phenyl carbonate sidechain, a phenyl ester sidechain, or an aliphatic ester sidechain; irradiating a solution containing the model compound with ultraviolet light, the solution containing methanol or ethanol; determining a first-order kinetic rate constant of the model compound; and identifying the aromatic ketone-containing moiety as a suitable endcapping agent for the crosslinkable polycarbonate if the first-order kinetic rate constant is at least 0.1 $min^{-1}$.

The solution may further include dichloromethane. In particular embodiments, the volume ratio of dichloromethane to the methanol or ethanol is about 80:20.

The solution is usually irradiated for a time of about 2 minutes to about 30 minutes. The solution can be irradiated with an ultraviolet light dosage of about 5 $J/cm^2$ to about 90 $J/cm^2$ of UVA radiation.

Also disclosed are crosslinkable polycarbonates formed from at least one dihydroxy compound and an aromatic ketone endcapping agent, wherein the aromatic ketone endcapping agent includes a moiety that has a first-order kinetic rate constant of at least 0.1 $min^{-1}$ as determined by: synthesizing a model compound containing (i) an aromatic ketone containing moiety and (ii) either a phenyl carbonate sidechain or an aliphatic ester sidechain; irradiating a solution containing the model compound with ultraviolet light, the solution containing methanol or ethanol; and determining a first-order kinetic rate constant of the model compound.

The polycarbonate is sometimes a bisphenol-A homopolymer. Other times, the polycarbonate is a copolymer and at least one dihydroxy compound is bisphenol-A.

Also disclosed are crosslinkable polycarbonates formed from at least one dihydroxy compound and a difunctional ketone monomer, wherein the difunctional ketone monomer has a first-order kinetic rate constant of at least 0.04 $min^{-1}$ as determined by: synthesizing a model compound containing (i) the difunctional ketone monomer and (ii) either a phenyl carbonate sidechain, an aromatic ester sidechain, or an aliphatic ester sidechain; irradiating a solution containing ethanol and the model compound with ultraviolet light; and determining a first-order kinetic rate constant of the model compound.

These and other non-limiting aspects of the present disclosure are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
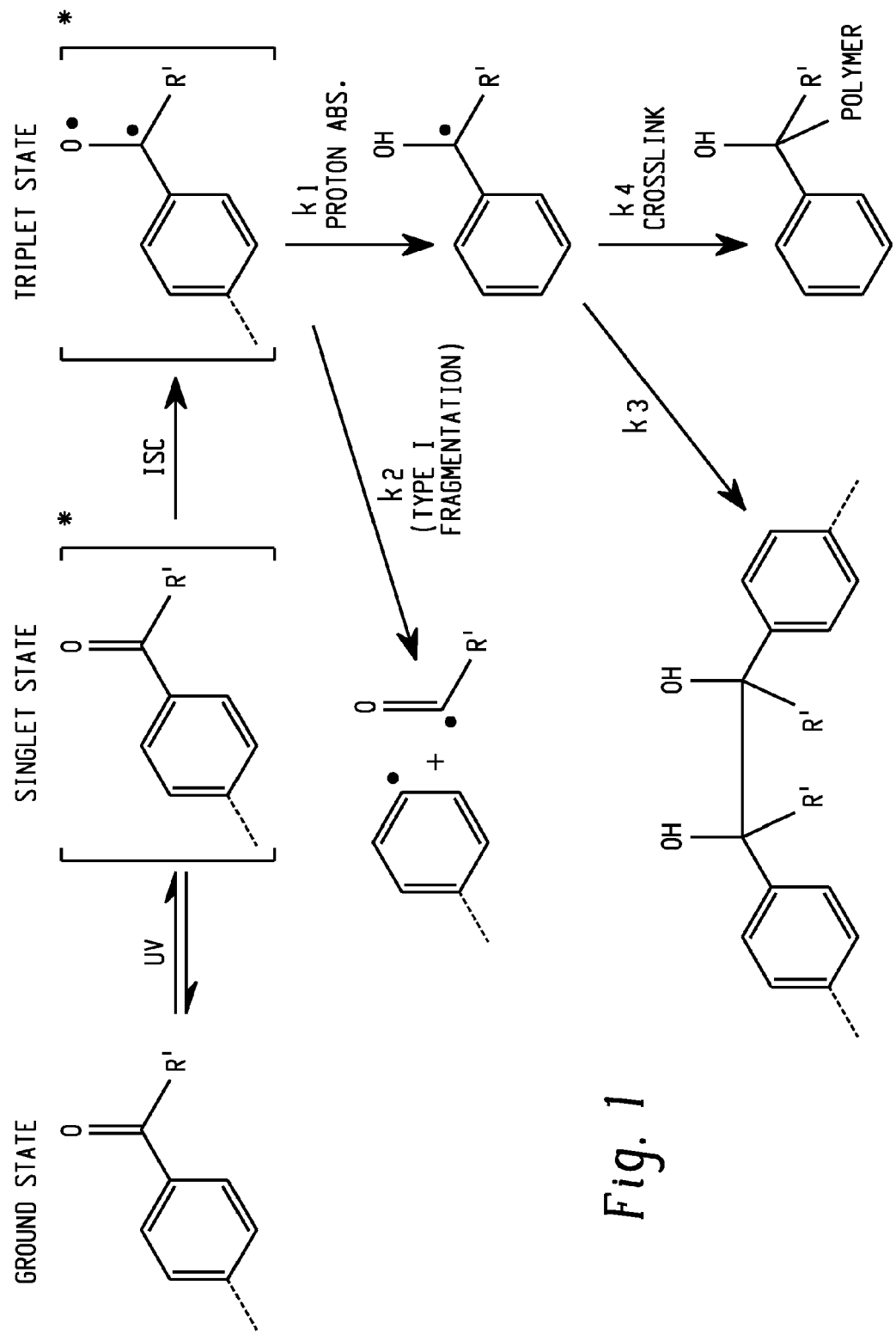
FIG. 1 is a diagram illustrating the mechanism by which carbonyl aromatic compounds usually undergo radical reactions.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

Numerical values in the specification and claims of this application, particularly as they relate to polymers or polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%. When the term "about" is applied to a ratio, the plus/minus 10% should be applied to the larger number. For example, "about 80:20" indicates a range of 72:28 to 88:12.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, the aldehyde group —CHO is attached through the carbon of the carbonyl group.

The term "aliphatic" refers to a linear or branched array of atoms that is not aromatic. The backbone of an aliphatic group is composed exclusively of carbon. The aliphatic group may be substituted or unsubstituted. Exemplary aliphatic groups include, but are not limited to, methyl, ethyl, isopropyl, hexyl, and cyclohexyl.

The term "aromatic" refers to a radical having a ring system containing a delocalized conjugated pi system with a number of pi-electrons that obeys Hückel's Rule. The ring system may include heteroatoms such as nitrogen, sulfur, selenium, silicon and oxygen, or may be composed exclusively of carbon and hydrogen. Aromatic groups are not substituted. Exemplary aromatic groups include, but are not limited to, phenyl, pyridyl, furanyl, thienyl, naphthyl and biphenyl.

The term "ester" refers to a radical of the formula —CO—O—, wherein the carbon atom and the oxygen atom are both covalently bonded to carbon atoms.

The term "acid halide" refers to a radical of the formula —CO—X, wherein the carbon atom is covalently bonded to another carbon atom.

The term "carbonate" refers to a radical of the formula —O—CO—O—, wherein the oxygen atoms are both covalently bonded to carbon atoms. Note that a carbonate group is not an ester group, and an ester group is not a carbonate group.

The term "hydroxyl" refers to a radical of the formula —OH, wherein the oxygen atom is covalently bonded to a carbon atom The term "alkyl" refers to a radical composed entirely of carbon atoms and hydrogen atoms which is fully saturated. The alkyl radical may be linear, branched, or cyclic.

The term "aryl" refers to an aromatic radical that is composed exclusively of carbon and hydrogen. Exemplary aryl groups include phenyl, naphthyl, and biphenyl. Note that "aryl" is a subset of aromatic.

The term "heteroaryl" refers to an aromatic radical having a ring system that is composed of carbon, hydrogen, and at least one heteroatom. Exemplary heteroaryl groups include pyridyl, furanyl, and thienyl. Note that "heteroaryl" is a subset of aromatic, and is exclusive of "aryl".

The term "halogen" refers to fluorine, chlorine, bromine, and iodine.

The term "hydrocarbon" refers to a radical which is composed exclusively of carbon and hydrogen. Both alkyl and aryl groups are considered hydrocarbon groups.

The term "amino" refers to a radical of the formula R—NH$_2$, wherein R is a carbon atom. For purposes of this disclosure, the amino group is a primary amino group, i.e. contains two hydrogen atoms.

The terms "carboxy" or "carboxyl" refers to a radical of the formula —COOH, wherein the carbon atom is covalently bonded to another carbon atom. It should be noted that for the purposes of this disclosure, a carboxyl group may be considered as having a hydroxyl group. However, it should be noted that a carboxyl group can participate in certain reactions differently from a hydroxyl group.

The term "oxyalkylene" refers to a divalent radical of the formula —(OR$^1$)$_m$—, wherein each R$^1$ is independently alkyl; m is an integer and is 1 or higher.

The term "substituted" refers to at least one hydrogen atom on the named radical being substituted with another functional group, such as halogen, —CN, or —NO$_2$. An aryl group may also be substituted with alkyl or alkoxy. Exemplary substituted aryl groups include methylphenyl and methoxyphenyl.

The term "copolymer" refers to a molecule derived from two or more structural unit or monomeric species, as opposed to a "homopolymer", which is a molecule derived from only one structural unit or monomer.

The term "crosslink" and its variants refer to the formation of a stable covalent bond between two polymers/oligomers. This term is intended to encompass the formation of covalent bonds that result in network formation, or the formation of covalent bonds that result in chain extension. The term "crosslinking agent" refers to a compound having the ability to form such stable covalent bonds.

Choosing a suitable crosslinking agent that can be used with a given polymer is not trivial. Several requirements must be met that will depend on the identity of the polymer, the type of application, and the type of processing which the polymer will undergo. The methods of the present disclosure provide data that is useful for screening and selecting suitable crosslinking agents, particularly those that can be used as endcapping agents or co-monomers with polycarbonate polymers. Those methods also include using the identified crosslinking agents in a polycarbonate polymer.

As used herein, the terms "polycarbonate" and "polycarbonate polymer" mean a polymer having repeating structural carbonate units of the formula (1):

(1)

in which at least about 60 percent of the total number of R$^1$ groups are aromatic organic radicals and the balance thereof are aliphatic, alicyclic, or aromatic radicals. An ester unit (—COO—) is not considered a carbonate unit, and a carbonate unit is not considered an ester unit. In one embodiment, each R$^1$ is an aromatic organic radical, for example a radical of the formula (2):

-A$^1$-Y$^1$-A$^2$-         (2)

wherein each of A$^1$ and A$^2$ is a monocyclic divalent aryl radical and Y$^1$ is a bridging radical having one or two atoms that separate A$^1$ from A$^2$. In an exemplary embodiment, one atom separates A$^1$ from A$^2$. Illustrative non-limiting examples of radicals of this type are —O—, —S—, —S(O)—, —S(O$_2$)—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical Y$^1$ may be a hydrocarbon group or a saturated hydrocarbon group such as methylene, cyclohexylidene, or isopropylidene. The term "polycarbonate" encompasses both homopolycarbonates and copolycarbonates.

Polycarbonates may be produced by the interfacial reaction of dihydroxy compounds having the formula HO—R$^1$—OH, wherein R$^1$ is as defined above. Dihydroxy compounds suitable in an interfacial reaction include, among others, the dihydroxy compounds of formula (3)

HO-A$^1$-Y$^1$-A$^2$-OH         (3)

wherein Y$^1$, A$^1$ and A$^2$ are as described above. Also included are bisphenol compounds of general formula (4):

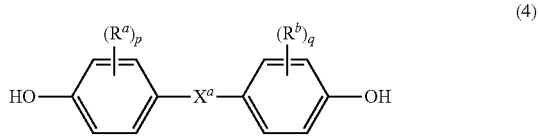

(4)

wherein $R^a$ and $R^b$ each represent a halogen atom or a monovalent hydrocarbon group and may be the same or different; p and q are each independently integers of 0 to 4; and $X^a$ represents one of the groups of formula (5):

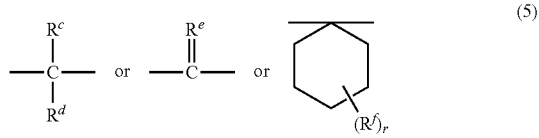

(5)

wherein $R^c$ and $R^d$ each independently represent a hydrogen atom or a monovalent linear or cyclic hydrocarbon group; $R^e$ is a divalent hydrocarbon group; $R^f$ is a monovalent linear hydrocarbon group; and r is an integer from 0 to 5.

Specific examples of the types of bisphenol compounds that may be represented by formula (3) include 1,1-bis(4-hydroxyphenyl) methane, 1,1-bis(4-hydroxyphenyl)ethane, 2,2-bis(4-hydroxyphenyl)propane (hereinafter "bisphenol-A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl) n-butane, 2,2-bis(4-hydroxy-1-methylphenyl)propane, 1,1-bis(4-hydroxy-t-butylphenyl) propane; 4,4'-(1-phenylethane-1,1-diyl)diphenol or 1,1-bis(4-hydroxyphenyl)-1-phenyl-ethane (bisphenol-AP); 1,1-bis(4-hydroxyphenyl)-3,3,5-trimethylcyclohexane) (bisphenol TMC); 1,1-bis(4-hydroxy-3-methylphenyl)cyclohexane (DMBPC); and 2,2-bis(3,5-dibromo-4-hydroxyphenyl)propane (tetrabromobisphenol-A or TBBPA). Depicted below is bisphenol-A, which is a commonly used monomer in polycarbonates.

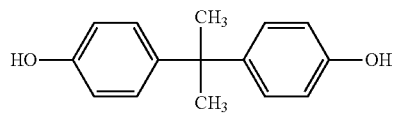

Generally, in the methods of the present enclosure, a crosslinker candidate is first identified. The crosslinker candidate can be a potential endcapping agent, or a potential monomer to be incorporated into the backbone of a polymer. An aromatic carbonate derivative, aromatic ester derivative, or aliphatic ester derivative of the crosslinker candidate is then synthesized to form an initial product (i.e. a product of the crosslinker candidate). The initial product is then tested to obtain measurements to determine the suitability of the crosslinker candidate as a crosslinking agent. It is noted that although measurements are made on the initial product, i.e. a derivative of the crosslinker candidate, they are intended to provide information on the crosslinker candidate itself. As a result, the present text may refer interchangeably to the "initial product" and the "crosslinker candidate."

In the methods of the present disclosure, a solution containing a known concentration of the initial product is then irradiated, and the decomposition of the initial product is measured. The first-order kinetic rate constant for the disappearance of the initial product can be determined. In some embodiments of the methods described herein, the suitability of the crosslinker candidate is determined by using only the first-order kinetic rate constant of the initial product. Where the first-order kinetic rate constant exceeds certain threshold values, the candidate is suitable as a crosslinkable monomer or endcapping agent.

Alternatively, if a first threshold amount of the initial product disappears during the irradiation, this is also a sign that the initial product crosslinked and so may be worthy of further consideration for use as a co-monomer, an endcapping agent, or a low molecular weight additive of the polymer. In embodiments, the first threshold amount is that at least 60% of the initial product disappeared during irradiation, or in other words that the starting amount of the initial product was reduced by at least 60% by the irradiation. It should be clear that if desired, determining both the first-order kinetic rate constant and the amount of the initial product that disappears can be done.

If the crosslinker candidate molecule exceeds the first threshold amount or has a sufficiently high first-order kinetic rate constant, then a secondary screening can occur. An article is formed from a polymer that contains the crosslinker candidate as an endcap or a co-monomer. The article is irradiated, and then (i) the increase in crosslink density, and/or (ii) the gel formation percentage of the article is also measured. Based on the first-order kinetic rate constant and either (i) the increase in crosslink density or (ii) the gel formation percentage, the suitability of the crosslinker candidate can be determined. In other embodiments, all three measurements (first-order kinetic rate constant, increase in crosslink density, and gel formation percentage) are used to determine the suitability of the crosslinker candidate. The term "crosslinker candidate" is used to refer to a molecule or moiety that is capable of crosslinking under irradiation at the appropriate wavelength. Generally, such molecules or moieties include a double bond, such as a ketone group (—CO—) or a vinyl group (—CH=CH—). Such molecules or moieties generally also include one or more reactive groups that can be used to form a covalent bond and join the molecule/moiety to another polymeric backbone. Such reactive groups may include a hydroxyl, amino, carboxyl, ester, or acid halide group. The crosslinker candidate generally includes one or more aromatic radicals, though crosslinker candidates may also contain aliphatic esters without an aromatic group. Some examples of crosslinker candidates include the hydroxyl-substituted forms of acetophenone, benzophenone, anthraquinone, coumarin, fluorenone, or stilbene.

Methods for identifying suitable crosslinking molecules are described in more detail in the following text. First, an aromatic carbonate, aromatic ester, or aliphatic ester derivative of the crosslinker candidate is synthesized to form an "initial product". Put another way, an aromatic carbonate, aromatic ester, or aliphatic ester group is attached as a sidechain to the crosslinker candidate. This aromatic ring/aliphatic ester models the presence of a polymer around the crosslinker candidate without needing to use actual polymer, which reduces research costs and research time for identifying useful crosslinking candidates. In particular embodiments, the aromatic carbonate is an aryl carbonate group or a heteroaryl carbonate group. In particular embodiments herein, the polymer being modeled is a polycarbonate polymer, and more specifically a polycarbonate having bisphenol-A monomer moieties.

Reactions for forming an aromatic carbonate as the initial product are generally known in the art, and can be done for example, by reacting a phenolic crosslinker candidate with phenyl chloroformate in dichloromethane and in the presence of a catalyst such as triethylamine (TEA), as illustrated below in Reaction 1. The reactions to form aromatic and aliphatic esters as the initial product can be done, for example, by reacting an acidic crosslinker candidate with ethanol and a catalytic amount of para-toluenesulfonic acid (p-TsOH) as illustrated below in Reaction 1-a.

Reaction 1:

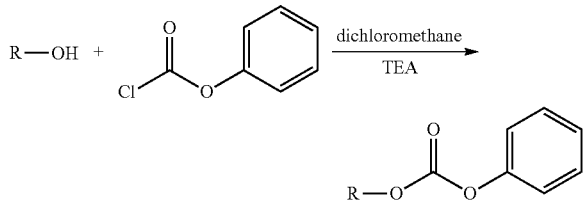

Reaction 1-a:

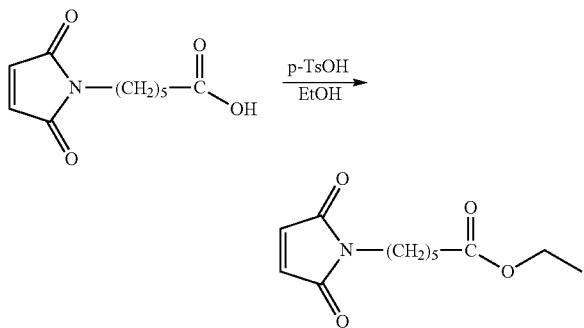

In more specific embodiments, the crosslinker candidate is a diaromatic ketone, or is a maleimide. A diaromatic ketone has the structure of Formula (I), and a maleimide has the structure of Formula (II), as illustrated below:

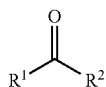 (I)

where $R^1$ and $R^2$ are independently aryl, and at least one of $R^1$ and $R^2$ is substituted with a sidechain containing a reactive group;

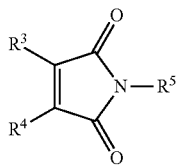 (II)

where $R^3$, $R^4$, and $R^5$ are independently hydrogen, halogen, alkyl, or aryl, and at least one of $R^3$, $R^4$, and $R^5$ is substituted with a sidechain containing a reactive group. Exemplary sidechains include oxyalkylene, alkyl, and substituted alkyl.

Next, a solution containing a known concentration of the initial product is irradiated for a first time period. The solution includes dichloromethane and a linear alkyl alcohol as solvents. In more specific embodiments, the linear alkyl alcohol is methanol or ethanol. The volume ratio of dichloromethane to the linear alkyl alcohol in the solution may be from about 70:30 to about 90:10, and may in specific embodiments be about 80:20.

The solution is irradiated with ultraviolet light. UV light has a wavelength between 10 nanometers and 400 nm. The first time period for which the solution is irradiated may be from about 10 minutes to about 60 minutes, and is generally sufficient for crosslinking to occur. A mercury arc lamp can be used for irradiation. It is contemplated that during the first time period, samples are periodically removed from the solution, so that a profile can be built up of the amount of initial product remaining in each sample. The solution is generally exposed to a dosage of about 30 J/cm$^2$ of UV radiation, more desirably at wavelengths of 280 nm to 450 nm.

The irradiation with UV light tests the capacity of the initial product to undergo radical-forming reactions. In this regard, carbonyl aromatic compounds usually undergo radical reactions by way of the general mechanism shown in FIG. 1. Starting at the left, UV exposure excites an electron from the ground state to the singlet state. Via intersystem crossing (ISC), the singlet state can nonradiatively transition to a triplet state. Absorption of a proton (reaction rate k1) leads to a intermediate radical, which can then react, either with another endcap (reaction rate k3) or with another part of a separate polymer chain (reaction rate k4). Alternatively, Type I fragmentation of the triplet state can occur (reaction rate k2), leading to two radicals which can then react with other radicals.

A first-order kinetic rate constant for the disappearance of the crosslinker candidate can then be determined. If multiple samples were taken during the first time period, this can be done relatively simply using the data that can be generated from those samples. The first-order kinetic equation is as follows:

$$\ln [C] = \ln [C_0] - k \cdot t$$

where [C] is the concentration of the crosslinker candidate at time t, [$C_0$] is the concentration of the crosslinker candidate before irradiation, and k is the first-order kinetic rate constant.

If the crosslinker candidate is a difunctional monomer, and the first-order kinetic rate constant (k) is at least 0.04 min$^{-1}$ when measured in a solution of 20% ethanol and 80% dichloromethane (v/v), then the crosslinker candidate may be identified as a suitable crosslinking agent. If the crosslinker candidate is a potential endcapping agent (i.e. a monofunctional molecule) and the first-order kinetic rate constant is at least 0.1 min$^{-1}$ when measured in a solution of 20% ethanol and 80% dichloromethane (v/v), then the crosslinker candidate may be identified as a suitable crosslinking agent.

Alternatively, another initial assessment is to determine whether a first threshold amount of the crosslinker candidate disappeared during the first time period. Generally, it is believed that the crosslinker candidate disappears due to a photochemical reaction (e.g. dimerization), and this is evident when using ultra-performance liquid chromatography (UPLC), or similar measurement methods. In UPLC, the area of the peak corresponding to the crosslinker candidate will decrease as the photochemical reaction occurs, and the area of the peak corresponding to the photochemical product will increase. In particular embodiments, the first threshold amount is a 60% decrease in the crosslinker candidate. Put another way, if 60% or more of the crosslinker candidate disappears after irradiation, the crosslinker candidate passes this initial screen and can then be subjected to polymerization and additional testing. In other words, after irradiation, the concentration of the crosslinker candidate should decrease down to 40% or more of its initial pre-irradiation value to be considered a good candidate for further screening. This determination of the first threshold amount can be performed in conjunction with the determination of the first-order rate constant, or can be used independently without determining the first-order rate constant.

Next, a polycarbonate polymer is synthesized which uses the crosslinker candidate in the form of an endcap or as a co-monomer. At least one article is molded or casted using the polymer, and the article is then irradiated with UV light for a specified dosage to induce cross-linking. It is contemplated that multiple articles are used, with an article being periodically removed from the irradiation, so that a sample can be taken and a profile can be built up of the effect of the irradiation upon the polymer. The irradiation may be constant, or may be spread over multiple irradiation periods. For example, during testing, the articles may be placed on a conveyor belt that passes underneath a UV lamp, and after being irradiated are placed again at the head of the conveyor belt to pass a given number of times beneath the UV lamp. In more specific embodiments, the article is an Izod bar having a thickness of 3.2 millimeters (mm).

The articles can then be measured to determine the increase in crosslink density x due to the UV exposure. The value of x is a function of the UV dosage and the amount of crosslinker candidate in the polymer. The value of x can be determined by dissolving the polycarbonate resin before and after UV exposure in an organic solvent and measuring the weight-average molecular weights (Mw) using gel permeation chromatography (GPC). The value of x can be determined using the formula:

$$Mw = \frac{Mw0}{1 - 2 \cdot n \cdot x}$$

wherein Mw0 is the weight average molecular weight of the polymer before irradiation; Mw is the weight average molecular weight of the polymer after irradiation; and n is the number of monomers for the given weight average molecular weight of the polymer before irradiation. Generally speaking, if the Mw of the polymer does not increase after irradiation, it is unlikely that crosslinking is occurring. An insoluble discreet gel is generally formed on the surface of the article when x is from 0.0012 to 0.0015. In particular embodiments, x should be at least 0.0012, or at least 0.0015. It is noted that the crosslink density is only useful up to the gel point where its value stops increasing. Hence, this method is useful for determining if branching or crosslinking is occurring, but not useful for determining how much gel can be produced by UV irradiation. In addition, for some molecules, visible gel structures that can be observed with the naked eye are not formed, but the presence of insoluble gels can be observed in concentrated solutions that swell. Such gelation can be considered a "pass" with regards to the increase in crosslink density.

Either alternatively to or in addition to measuring the increase in crosslinking density, the gel formation percentage of the article after UV exposure can be used to measure the amount of crosslinking that has occurred. The article is first weighed and then exposed to dichloromethane, which permits the soluble portion of the article to dissolve, leaving behind an insoluble gel. After collecting and drying the insoluble gel fraction, the dried gel is weighed, and the weight percentage is determined. A typical value for gel formation percentage is 5% (weight/weight basis) or higher, including 6%, on a 3.2 mm thick Izod bar with a weight of at least 2.9 grams, to identify the crosslinker candidate as a suitable crosslinking agent. It is noted that the gel formation percentage depends on the shape and thickness of the article because the crosslinking is a surface phenomenon dependent on the depth to which the UV irradiation penetrates.

A typical crosslinker candidate is identified as a suitable crosslinking agent for use with polycarbonate polymers when (i) a threshold amount of 60% of the initial product (i.e. crosslinker candidate) disappears during the irradiation of the first time period, and (ii) either (a) the increase in crosslink density is at least 0.0012 or (b) the gel formation percentage is at least 6%.

In some more specific embodiments, the crosslinker candidate is identified as a suitable crosslinking agent for use with polycarbonate polymers when (i) the first-order kinetic rate constant is at least 0.1 $min^{-1}$ when measured in a solution of 20% ethanol and 80% dichloromethane (v/v); (ii) a threshold amount of 60% of the initial product (i.e. crosslinker candidate) disappears during the irradiation of the first time period; (iii) the increase in crosslink density is at least 0.0012; and (iv) the gel formation percentage is at least 6%.

Crosslinker candidates can be identified as suitable crosslinking agents if they pass the tests described herein; otherwise, they are considered to be unsuitable. The suitable crosslinking agent can then be incorporated into a polycarbonate polymer, either as an endcapping agent or as a co-monomer. Such polycarbonates can be manufactured by processes known in the art, such as interfacial polymerization and melt polymerization. Although the reaction conditions for interfacial polymerization may vary, an exemplary process generally involves dissolving or dispersing one or more phenolic reactants (i.e. dihydroxy monomers and monohydroxy endcapping agent) in aqueous caustic soda or potash, adding the resulting mixture to a suitable water-immiscible solvent medium, and contacting the reactants with a carbonate precursor in the presence of a suitable catalyst such as triethylamine or a phase transfer catalyst, under controlled pH conditions, e.g., about 8 to about 10. Generally, in the melt polymerization process, polycarbonates may be prepared by co-reacting, in a molten state, the dihydroxy reactant(s) and a diaryl carbonate ester, such as diphenyl carbonate, in the presence of a transesterification catalyst in a Banbury® mixer, twin screw extruder, or the like to form a uniform dispersion. Volatile monohydric phenol is removed from the molten reactants by distillation and the polymer is isolated as a molten residue.

Polymeric compositions may be made that include the polycarbonate polymer including the suitable crosslinking agent. Other polymeric base resins may also be added into the composition, along with other additives.

The polymeric composition/blends of the present disclosure, containing the polycarbonate polymer with the suitable crosslinking agent, can then be formed into an article by a variety of known processes such as solution casting, profile extrusion, film and/or sheet extrusion, sheet-foam extrusion, injection molding, blow molding, thermoforming, and the like. The article is then exposed to ultraviolet (UV) light at an appropriate wavelength and in an appropriate dosage that brings about the desired amount of crosslinking for the given application. Depending on the end use application and the desired properties, the UV exposure can be performed on one or more surfaces of the article.

The compositions/blends can be molded into useful shaped articles by a variety of means such as injection molding, overmolding, co-injection molding, extrusion, multilayer extrusion, rotational molding, blow molding and thermoforming to form articles. Exemplary articles include a film, a sheet, a layer of a multilayer film, or a layer of a multilayer sheet.

The resulting articles, containing the suitable crosslinking agent, can then be irradiated at sufficient times and/or intensities to induce crosslinking. The irradiation is usually by ultraviolet (UV) light, which has a wavelength of 10 nanometers (nm) to 400 nm, or in more specific ranges from about 330 nm to about 380 nm, or from about 280 nm to about 360 nm. For example, the crosslinking can be accomplished by using a UV-emitting light source such as a mercury vapor, High-Intensity Discharge (HID), or various UV lamps. Commercial UV lamps are sold for UV curing from manufacturers such as Fusion UV. Non-limiting examples of UV-emitting light bulbs include H bulbs, D bulbs, H+ bulbs, and V bulbs. An H bulb has strong output in the range of 200 nm to 320 nm. The D bulb has strong output in the 320 nm to 400 nm range. The V bulb has strong output in the 400 nm to 420 nm range. The light can also be filtered to remove harmful or unwanted wavelengths of light.

UV wavelengths can be separated into four different categories. UVA refers to wavelengths from 320 nm to 390 nm. UVB refers to wavelengths from 280 nm to 320 nm. UVC refers to wavelengths from 250 nm to 260 nm. UVV refers to wavelengths from 395 nm to 445 nm. These wavelengths of light were measured with an EIT Power-Puck, and the categories are defined by the manufacturer (EIT Inc., Sterling, Va.).

In particular embodiments, the articles are exposed to a selected UV light range having wavelengths from about 280 nanometers (nm) to about 380 nm, or from about 330 nm to about 380 nm, or from about 280 nm to about 360 nm, or from about 330 nm to about 360 nm. The wavelengths in a "selected" light range have an internal transmittance of greater than 50%, with wavelengths outside of the range having an internal transmittance of less than 50%. The change in transmittance may occur over a range of 20 nm. Reference to a selected light range should not be construed as saying that all wavelengths within the range transmit at 100%, or that all wavelengths outside the range transmit at 0%.

In some embodiments, the UV radiation is filtered to provide exposure to UVA radiation with no detectable UVC radiation, as measured using an EIT PowerPuck. The effective dosage can range from at least 1 J/cm$^2$ of UVA radiation up to about 60 J/cm$^2$ of UVA radiation. In more specific embodiments, the UV radiation is filtered to provide an effective dosage at least 2 J/cm$^2$, or at least 3 J/cm$^2$, or at least 12 J/cm$^2$, or at least 21 J/cm$^2$, or at least 36 J/cm$^2$ of UVA radiation, with no detectable UVC radiation, as measured using an EIT PowerPuck. In particular embodiments, the polycarbonate fibers are exposed to a dosage of about 21 J/cm$^2$ to about 60 J/cm$^2$ of UVA radiation, or in more particular embodiments a dosage of about 21 J/cm$^2$ to about 36 J/cm$^2$ of UVA radiation.

The following examples are provided to illustrate the methods of the present disclosure. The examples are merely illustrative and are not intended to limit the disclosure to the materials, conditions, or parameters set forth therein.

EXAMPLES

Photochemical irradiation of carbonate derivatives in a solution was performed using a reactor assembly from AceGlass Inc. (part number 7840-185). The assembly was composed of: a borosilicate glass reactor (1 L, unjacketed) with one 60/40 center joint, one 14/20 angled joint for sparger tube, one 24/40 vertical joint for condenser, and one #7 Ace-Thred for a thermometer. The UV lamp was a medium pressure quartz mercury-vapor lamp (450 W, approx. 5 inches arc length, part number 7825-34) and was located in the reactor, inside of a quartz immersion well (part number 7854-25 or 7854-27). To run the reaction, a quartz cell cuvette was used to hold the solution (Systems LLC, Cuvette Stoppered, 10 mm; Fisher Scientific. Catalog No.: 50-923-635). During the photochemical reaction, the cell wall was in direct contact with the outer wall of the reactor. At different time points, the UV lamp was stopped and a sample was taken and analyzed.

The energy distribution for the energy lamp is shown in the table below.

| UV Region | Energy on the quartz cuvette (mW/cm$^2$). Water filtered. | Total Energy (Watts, total length of the lamp) |
|---|---|---|
| UV-A | 49 | 28.0 |
| UV-B | 11 | 28.7 |
| UV-C | 0 | 29.4 |

Liquid chromatography analysis (UPLC) of all the samples was performed using a Waters Acquity system (from Ultra Performance LLC) with a binary solvent manager, injector and PDA (Photo Diode Array) detector. The chromatography column used was from Phenomenex, a Kinetex 1.7 μm XB C-18 100A (50×2.10 mm); Part number: 00B-4498-AN. The system was composed of a gradient used is shown in Table A.

TABLE A

| Time (min.) | Flow Rate | % A (Water) | % B (Acetonitrile) |
|---|---|---|---|
| Initial | 0.8 | 65.0 | 35.0 |
| 0.45 | 0.8 | 51.0 | 49.0 |
| 0.50 | 0.8 | 50.0 | 50.0 |
| 1.20 | 0.8 | 10.0 | 90.0 |
| 1.40 | 1.2 | 0.0 | 100.0 |
| 1.75 | 1.2 | 0.0 | 100.0 |
| 1.80 | 0.8 | 65.0 | 35.0 |
| 2.50 | 0.8 | 65.0 | 35.0 |
| 7.50 | 0.8 | 65.0 | 35.0 |
| 10.01 | 0.05 | 50.0 | 50.0 |

Samples were sometimes exposed to various doses of either filtered or unfiltered UV light. The unfiltered light was provided by a Fusion UV conveyor system, which used a D-bulb electrodeless bulb. The filtered light was provided by a Loctite Zeta 7411-S system, which used a 400 W metal halide arc lamp and behaved like a D-bulb electrodeless bulb in spectral output with a 280-nm cut-on wavelength filter. The UV energy (for given exposure time, or per pass) for each system is provided below in Table B and Table C, and was measured using an EIT PowerPuck. The dose was measured as the energy from 320-390 nm (UVA)), 280-320 nm (UVB), 250-260 nm (UVC) and 395-445 nm (UVV). The dose was calculated in J/cm$^2$.

TABLE B

Loctite (filtered light).

| Filtered | Loctite Dose | | | |
|---|---|---|---|---|
| | UVA J/cm² | UVB J/cm² | UVC J/cm² | UVV J/cm² |
| 160 sec | 6 | | | |
| 320 sec | 12 | 2.4 | 0 | 7.3 |
| 480 sec | 18 | | | |
| 640 sec | 24 | | | |
| 800 sec | 30 | | | |
| 960 sec | 36 | 7.2 | 0 | 21.9 |

TABLE C

Fusion (unfiltered light)

| Unfiltered | Fusion UV | | | |
|---|---|---|---|---|
| | UVA J/cm² | UVB J/cm² | UVC J/cm² | UVV J/cm² |
| 1 pass | 6 | | | |
| 2 passes | 12 | 3.7 | 0.45 | 5.8 |
| 3 passes | 18 | | | |
| 4 passes | 24 | | | |
| 5 passes | 30 | | | |
| 6 passes | 36 | 11.0 | 1.34 | 17.5 |
| 7 passes | 42 | | | |
| 15 passes | 90 | | | |
| 20 passes | 120 | | | |
| 25 passes | 150 | | | |

Example 1

Reaction Process 1 for Making Crosslinking Candidates

Ten (10) different molecules containing phenolic functionalities were tested for their suitability as crosslinking agents for polycarbonate. The moieties were first reacted according to Reaction Process 1 to obtain phenyl carbonate derivatives that were tested (i.e. initial products).

An exemplary procedure for Reaction Process I is the preparation of 4-O-phenylcarbonate coumarin, described as follows: In a dry 500 mL round bottom flask, 25 grams (154.2 mmol) of 4-hydroxycoumarin were suspended in 200 mL of dichloromethane. After addition of 23.6 mL (169.6 mmol, 1.1 eq) of triethylamine, the compound completely solubilized. After solubilization, 20.3 mL (161.9 mmol, 1.05 eq) of phenylchloroformate was added dropwise at room temperature. The reaction was followed by UPLC. After total consumption of starting material, HCl (0.2 M, 100 mL) was added to quench the reaction. The crude was further extracted with HCl (0.2 M, 3×100 mL) and washed with distilled water (3×100 mL). The organic phase was dried with MgSO₄, filtered and evaporated at low pressure. The 4-O-phenylcarbonatecoumarin was obtained as a white pale-yellow solid (42.1 grams, 97% yield).

The 10 molecules, and the melting points of their phenyl carbonates, are illustrated in Table D.

TABLE D

| Molecule | m.p. of phenyl carbonate derivative (° C.) |
|---|---|
| 4-hydroxyacetophenone | 40.0-43.0 |
| 4-hydroxybenzophenone | 133.5 |
| 1-hydroxyanthraquinone | 73.4 |
| 7-hydroxycoumarin | 149.1 |
| 4-methyl-7-hydroxycoumarin | 72.5 |
| 4-hydroxycoumarin | 108.6 |
| 2-hydroxy-9-fluorenone | Not measured |
| 4,4'-dihydroxybenzophenone | 200.9 |

TABLE D-continued

| Molecule | m.p. of phenyl carbonate derivative (° C.) |
|---|---|
| 4-hydroxystilbene | Not measured |
| 3-methoxy-4-hydroxyacetophenone | 59.0 |
| 2,4-dihydroxybenzophenone | Not measured |

UV Results for Reaction Process I Crosslinking Candidates

A calibration curve was measured for some of these compounds, and is presented in Table E below. The calibration curve was obtained by analyzing the solutions with a UPLC device equipped with an LED array ($\lambda$=264 nm).

TABLE E

| Compound | Calibration curve | $\lambda$ (nm) | Range (mM) |
|---|---|---|---|
| (4-hydroxyacetophenone) | A = 259730 · [C] − 37957 | 264 | 0.10-4.59 |
| (4-hydroxybenzophenone) | A = 833759 · [C] + 130915 | 264 | 0.13-3.81 |
| (1-hydroxyanthraquinone) | A = 1991873 · [C] + 105430 | 264 | 0.15-4.38 |
| (4-hydroxycoumarin) | A = 241367 · [C] − 19770 | 264 | 0.08-6.02 |

A is the absorbance, and [C] is the concentration of the compound in mM. In this regard, the concentration range over which the calibration curve was obtained had to satisfy the following criteria: the area of the peak belonging to the compound had to follow a first-order polynomial function before and after irradiation for 30 minutes when analyzed at 264 nm.

Next, the phenyl carbonate derivatives were irradiated with UV light from a mercury arc lamp to test their capacity to undergo radical-forming reactions. A typical radical reaction experiment was performed as follows. A 20 mM solution of 4-O-hydroxybenzophenone phenyl carbonate in dichloromethane (DCM)/methanol (80:20, v/v) was made. The solution was irradiated for a given time period (2 minutes to 30 minutes) using the AceGlass setup described above. Samples (50 μL in 1000 μL of methanol) were periodically taken and analyzed by UPLC and quantified by UV ($\lambda$=264 nm) using the Waters Acquity system described above. This results in a UV dosage of about 5 J/cm$^2$ to about 90 J/cm$^2$ of UVA radiation.

In performing the experiment, the phenyl carbonate derivative (20 mM solution in dichloromethane/methanol (DCM/MeOH) or dichloromethane/ethanol (DCM/EtOH)) was placed in a quartz cell and irradiated for 30 minutes using the AceGlass setup described above.

If more than 60% of the initial product disappeared after irradiation, the crosslinker candidate was identified as a potentially useful crosslinking agent.

Of all the candidates shown above, the phenyl carbonate derived from 4-hydroxybenzophenone was the only crosslinking candidate that met the criterion of 60% disappearance of the initial product.

The first order kinetics of decomposition for acetophenone phenyl carbonate and benzophenone phenyl carbonate and anthraquinone phenyl carbonate were determined in two different solutions, DCM/MeOH (80:20, v/v) and DCM/EtOH (80:20, v/v). The first order kinetics of decomposition for 4-hydroxybenzophenone phenyl carbonate and anthraquinone phenyl carbonate were determined in the DCM/EtOH solution. The results are presented in Table 1. As seen here, the first-order kinetic rate constant is higher when ethanol was used. In addition, the benzophenone phenyl carbonate first order kinetic constant is higher than the one for acetophenone phenyl carbonate. This means that benzophenone reacts faster than acetophenone.

TABLE 1

| Derivative | DCM/MeOH (80:20) | DCM/EtOH (80:20) |
|---|---|---|
| phenyl (4-acetylphenyl) carbonate | k~0 min$^{-1}$ | k = 0.0165 min$^{-1}$ |
| benzophenone phenyl carbonate | k = 0.218 min$^{-1}$ | k = 0.227 min$^{-1}$ |
| 2-hydroxy-4-(phenoxycarbonyloxy)benzophenone | -NA- | k < 0.0165 min$^{-1}$ |
| anthraquinone phenyl carbonate | -NA- | * |

* Could not be measured due to degradation of molecule upon irradiation

Figure 2:
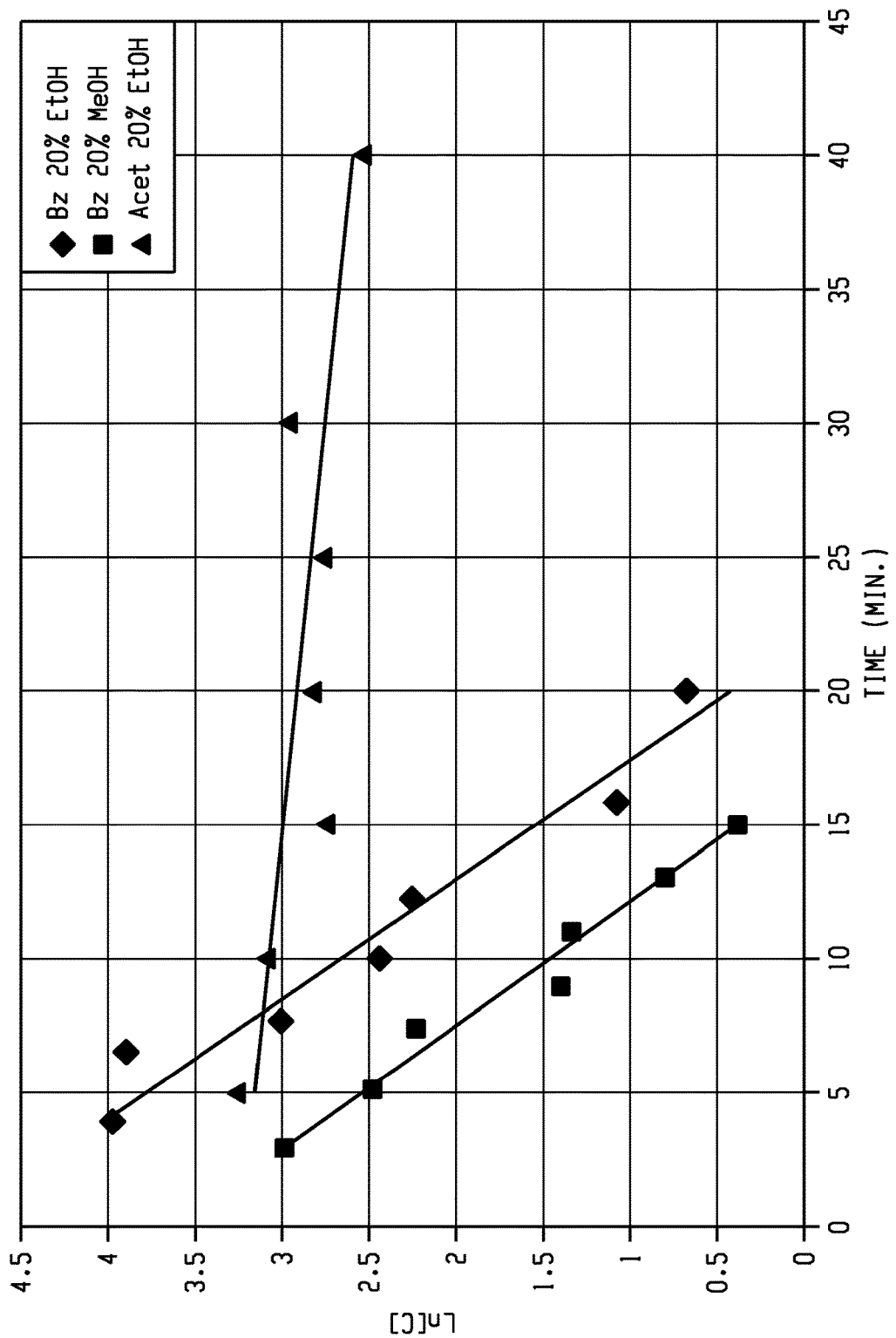
FIG. 2 is a graph showing the absorbance versus time for three test solutions, illustrating the use of the first-order kinetic rate constant. "Bz 20% EtOH" is a 40 mM solution of 4-hydroxybenzophenone phenyl carbonate in EtOH:DCM (20:80) irradiated using the AceGlass photochemical reactor. "Bz 20% MeOH" is a 40 mM solution of 4-hydroxybenzophenone phenyl carbonate in MeOH:DCM (20:80) irradiated using the AceGlass photochemical reactor. "Acet 20% EtOH" is a 40 mM solution of 4-(ethoxycarbonylmethoxy)benzophenone in EtOH:DCM (20:80) irradiated using the AceGlass photochemical reactor.

The results in Table 1 are also presented in FIG. 2. FIG. 2 is a graph showing the natural log (ln) of [C] versus time for the benzophenone phenyl carbonate (labeled Bz) in both the 20% ethanol and the 20% methanol solutions. Also shown is the ln of [C] versus time for the acetophenone phenyl carbonate derivative (labeled Acet) in 20% ethanol solution.

Polycarbonate Crosslinking Evaluations of Reaction 1 Process Candidates

Next, a polycarbonate polymer was synthesized using 4-hydroxybenzophenone (4-HBP) as an endcap structure. In a typical polymerization process, 30 grams of bisphenol-A (131 mmol) were suspended in a mixture of dichloromethane and water (500 mL and 300 mL respectively). Triethylamine (0.37 mL, 2.6 mmol, 2% mol/mol) and end-cap (4-hydroxybenzophenone, 0.65 grams; 3.3 mmol, 2.5% mol/mol) were added. Phosgene was bubbled through the solution at a 2 grams/minute rate and the pH was maintained at pH~9.5 for 12 minutes. After polymerization, the organic phase was washed with 800 mL of HCl 1 M and washed 5 times with distilled water. The polymer was precipitated on hot water, filtered and dried. Mw=31767, PDI=4.20 (2.5% mol/mol of benzophenone functionality as end-cap).

The end-capped polycarbonate derived from 4-hydroxybenzophenone thus obtained was blended down with a bisphenol-A homopolymer (Mw~30,000, MFR=7 g/10 min) using p-cumylphenol endcaps in order to vary the total amount of benzophenone content in various blends. Films were then made from the various blends. The films were prepared by dissolving the polymer blends in an organic solvent (dichloromethane) and solvent casting. An alternative way of preparing the films was to mix both polymers in the desired proportion and then hot press the powder at 50 psi at 515° F. for 30 seconds.

Next, the films were irradiated by passing them under the UV lamp (D-bulb) of a LC-6B Fusion UV Systems Inc. conveyor or using the Loctite® Zeta 4711-S system to expose the films to different dosages of UV energy. The films were then analyzed by gel permeation chromatography (GPC) and gel quantification was performed.

The increase in crosslink density (X) as a function of UV dosage and the mole percentage of 4-HBP in the blend is shown in Table 2 below.

TABLE 2

| 4-HBP (% mol) | "X" Factor vs. Energy (J/cm²) Energy (J/cm²) | | | | | | |
|---|---|---|---|---|---|---|---|
| | 0 | 6 | 12 | 18 | 24 | 30 | 36 | 42 |
| 0.23% | 0 | 0.00024 | 0.000475 | 0.000584 | 0.000654 | 0.000826 | 0.0009 | 0.0007 |
| 0.33% | 0 | 0.000231 | 0.000602 | 0.000782 | 0.000811 | 0.000918 | 0.000995 | 0.001066 |
| 0.42% | 0 | 0.000473 | 0.000871 | 0.00099 | 0.001059 | 0.00096 | 0.001146 | 0.001049 |
| 0.65% | 0 | 0.000432 | 0.000733 | 0.001185 | 0.001003 | 0.001067 | 0.001006 | 0.001063 |
| 0.83% | 0 | 0.00079 | 0.000918 | 0.001118 | 0.001206 | 0.001221 | 0.00118 | 0.001207 |
| 1.25% | 0 | 0.001055 | 0.001274 | 0.001287 | 0.001404 | 0.001746 | 0.001785 | 0.001796 |
| 2.50% | 0 | 0.001254 | 0.001867 | 0.002095 | 0.00224 | 0.002326 | 0.002368 | 0.002175 |

Figure 3:
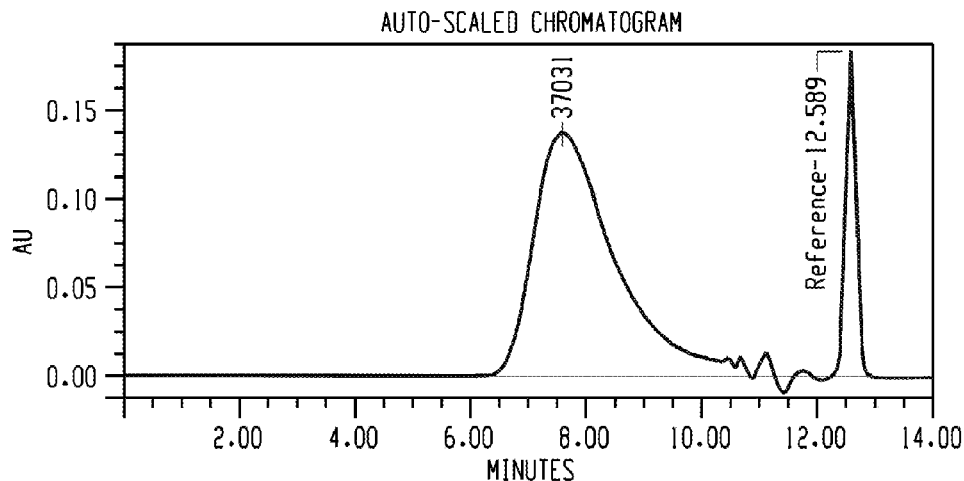
FIG. 3 shows the GPC chromatograms at zero and after 36 J/$cm^2$ UV irradiation for a neat bisphenol-A homopolycarbonate containing 4% 4-hydroxybenzophenone endcaps (i.e. not blended). The irradiated part was a film obtained by solvent casting. After UV irradiation, 100 mg of the film was dissolved in GPC solution for analysis. Absorbance units are on the y-axis and time in minutes is on the x-axis. The light source for the irradiation came from a Loctite® Zeta 7411-S.
Figure 3:
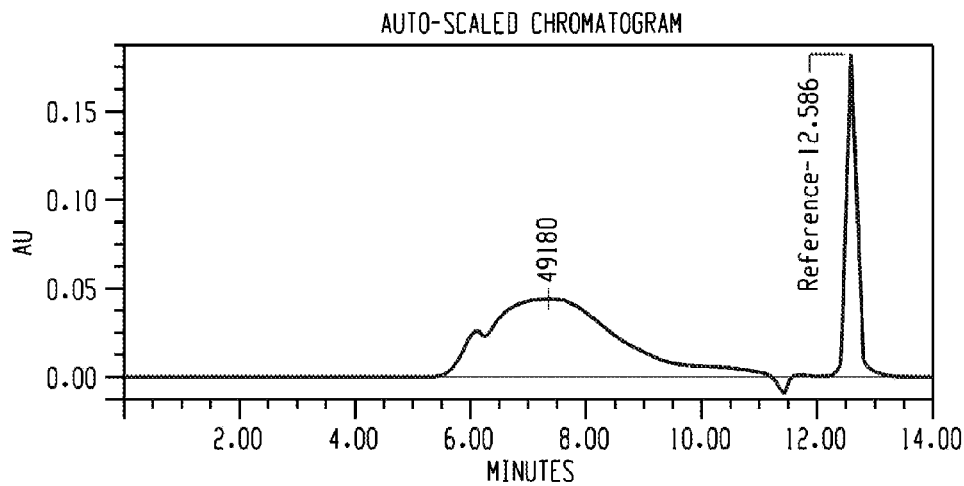

FIG. 3 shows the GPC chromatograms at zero and after exposure to 30 J/cm² of UVA energy. The increase in PDI and the increase in Mw can be seen.

Figure 4:
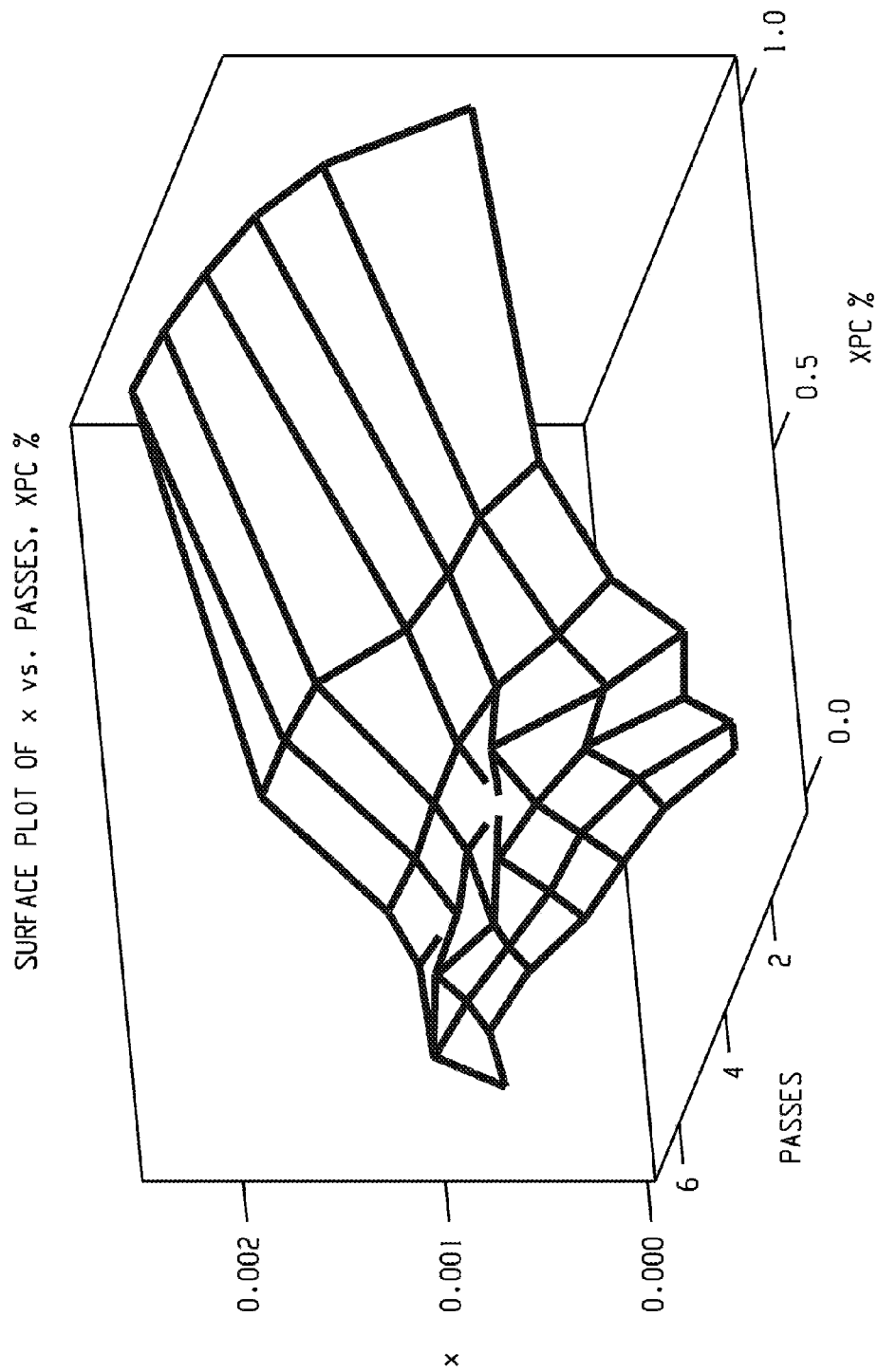
FIG. 4 is a surface plot showing the increase in crosslink density x versus the UV dose in J/$cm^2$ and the amount of 4-hydroxybenzophenone present in the test sample. The test sample is a film formed from a blend of (1) a bisphenol-A polycarbonate homopolymer with p-cumylphenol endcaps and (2) a bisphenol-A polycarbonate homopolymer containing 4% 4-hydroxybenzophenone endcaps. The amounts of each polymer were varied to obtain a range of 0.36% to 4% mol/mol of 4-hydroxybenzophenone in the blend.

FIG. 4 is a surface plot showing the increase in crosslink density x versus energy dosage and the molar percentage of benzophenone present in the blends shown in Table 2. According to this plot, a single piece of gel is formed when x is between 0.0012 and 0.0015, and this is the point where the crosslinked polycarbonate is considered to be optimal.

Figure 5:
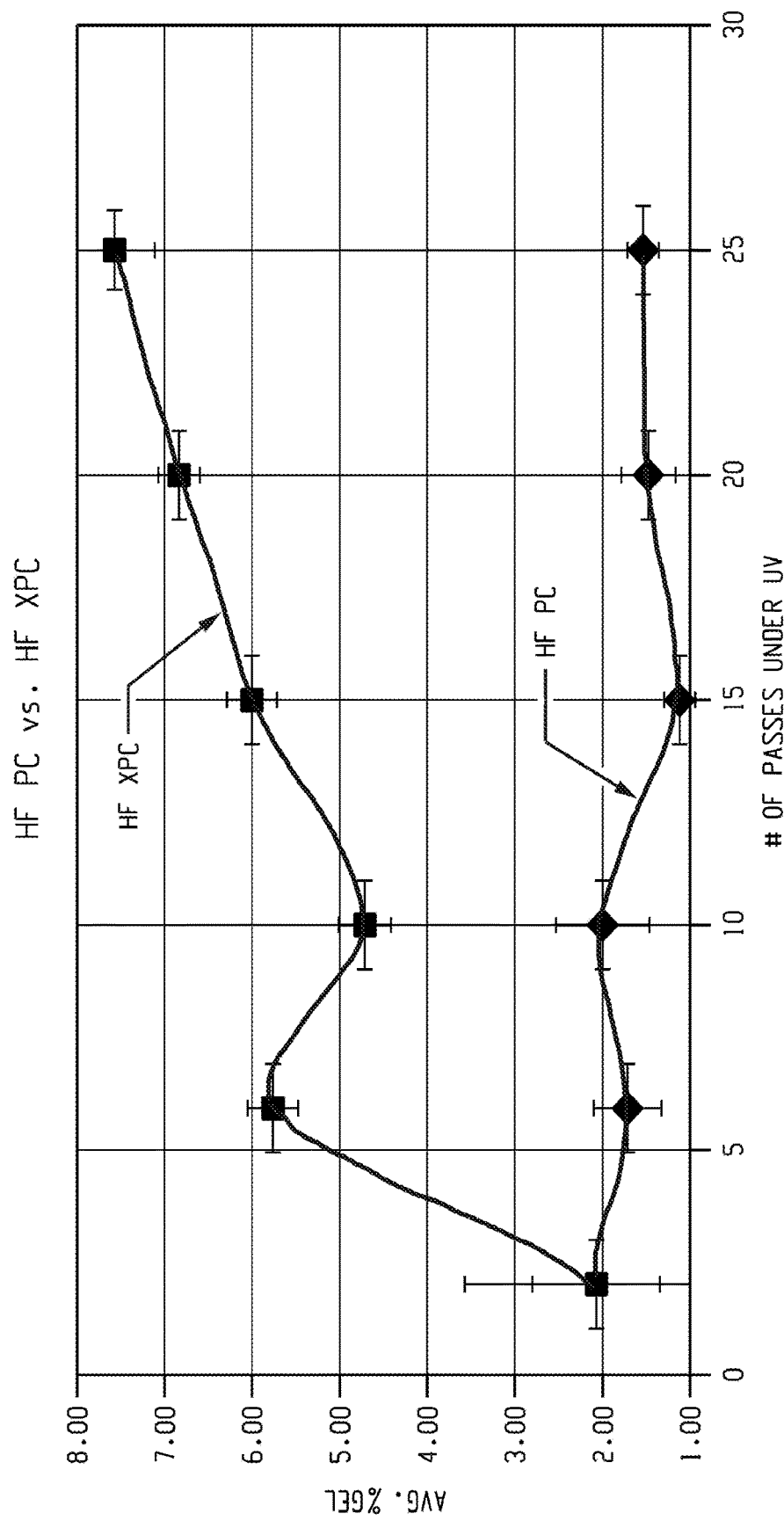
FIG. 5 is a graph showing the gel percentage versus UV dosage for two polycarbonates. One is a bisphenol-A homopolycarbonate having p-cumylphenol endcap and a Mw~21,000 (HF PC), and the other is a bisphenol-A homopolycarbonate having a 4-hydroxybenzophenone endcap (4% mol/mol) with a Mw~21,000 (HF XPC).

Finally, the gel formation percentage was determined by taking each film and dissolving soluble polycarbonate in dichloromethane (DCM), leaving the insoluble gel behind. FIG. 5 shows one set of results. Two lines are provided here. HF PC is the control sample, which used standard bisphenol-A polycarbonate using p-cumylphenol (PCP) as the endcap (Mw~21,000). HF XPC is the bisphenol-A polycarbonate containing 4 mol % of 4-hydroxybenzophenone as the endcap (Mw~21,000). The amount of gel was much higher with the the benzophenone endcap.

The k value for 4-HBP was very high, and it was the only molecule that had at least a 60% decomposition rate. The X measurement and the % gel both confirmed that crosslinking occurred when 4-HBP was used as an endcap. These results suggest that even when formed into articles having different shapes than a film, crosslinking will still occur with the polycarbonate polymer.

Table 3 provides the results of using several of the molecules of Table D as an end-cap structure in a bisphenol-A polycarbonate.

TABLE 3

| Molecule | Did gel form in solution? | Was gel content measured? |
|---|---|---|
| 4-hydroxyacetophenone | N | N |
| 4-hydroxybenzophenone | Y | Y |
| 1-hydroxyanthraquinone | N | N |
| 7-hydroxycoumarin | N | N |
| 4-methyl-7-hydroxycoumarin | N | N |
| 4-hydroxycoumarin | N | N |
| 2-hydroxy-9-fluorenone | N | N |
| 4,4'-dihydroxybenzophenone | Y | N |
| 4-hydroxystilbene | N | N |
| 3-methoxy-4-hydroxyacetophenone | N | N |

Example 2

Reaction Process 2 for Making Crosslinking Candidates

The following two compounds A and B were made by reacting a phenolic functionality with ethyl bromoacetate, dissolved in dimethylformamide (DMF) with potassium carbonate.

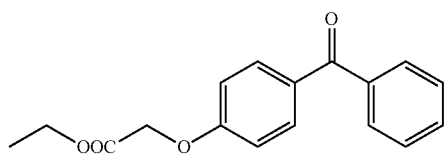

A

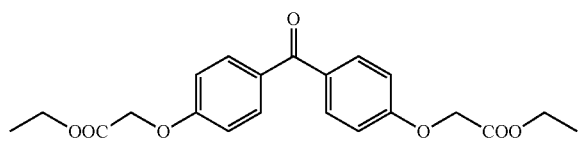

B

The procedure for preparing the ethyl ester derivative of 4-hydroxybenzophenone (compound A) was as follows: 12 grams (60.54 mmol) were suspended in 250 mL of DMF. 8 grams of potassium carbonate (1.1 equivalents) were added at room temperature. Next, 7.4 mL of ethyl bromoacetate (66.6 mmol, 1.1 equivalents) were added and allowed to react overnight. The work-up was performed by the addition of 200 mL of ethyl acetate and 500 mL of water. The aqueous phase was extracted after washing with 3×200 mL of ethyl acetate. The combined organic phases were then washed with 4×100 mL of water and 2×150 mL of saturated sodium chloride solution. After drying with magnesium sulfate and crystallization with chloroform, 17.0 grams (98% yield) of product were obtained. Compound A had a melting point of 84.4° C.

The procedure for preparing the disubstituted ethyl ester derivative of 4,4'-dihydroxybenzophenone (compound B) was as follows. 12.5 grams (58.25 mmol) of 4,4'dihydroxybenzophenone were suspended in 250 mL of DMF with 24.2 grams (2.5 equivalents) of potassium carbonate. After dissolution, 14.2 mL (128.15 mmol, 2.2 equivalents) of ethyl bromoacetate were added and stirred overnight at room temperature. The product was washed with 200 mL of ethyl acetate and 500 mL of water. An additional 3×200 mL of ethyl acetate was run through the aqueous phase and the aqueous phase extracted. The combined organic phases were further cleaned with 4×100 mL of water and 2×150 mL of saturated sodium chloride. After drying with magnesium sulfate and crystallization with chloroform, 18.05 grams (82% yield) of product were obtained. Compound B had a melting point of 117.5° C.

Example 3

Methods for Making Maleimidophenol Crosslinking Candidates

Compound C is the phenyl carbonate of 4-maleimidophenol, or phenyl [4-(2,5-dioxopyrrol-1-yl)phenyl]carbonate:

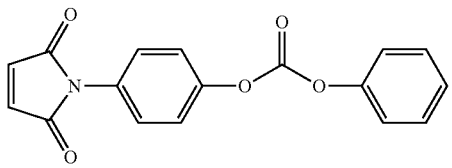

C

The procedure for preparing the phenyl carbonate of 4-maleimidophenol (compound C) was as follows. 20 grams (105.7 mmol) of maleimidophenol were suspended in 300 mL of dichloromethane. TEA (17 mL, 1.2 equivalents) was added as a base. At room temperature, 14.6 mL of phenyl chloroformate (1.1 equivalents) were added into the reactor dropwise. After three hours of reaction, the solution was washed with 3×100 mL of HCl 1M and 3×50 mL of saturated sodium bicarbonate solution, followed by 2×100 mL of saturated sodium chloride solution. The organic phase was then dried with magnesium sulfate. The organic phase was evaporated, and 29 grams (97% yield) of a yellow solid were obtained. The melting point of Compound C was 158.3° C.

Compound D is the ethyl ester derivative of 6-maleimidohexanoic acid:

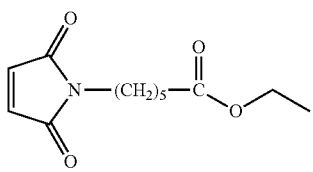

D

The procedure for preparing the ethyl ester derivative of 6-maleimidohexanoic acid (compound D) was as follows. 5 grams (23.7 mmol) of 6-maleimidohexanoic acid were dissolved in 100 mL of ethanol, and a catalytic amount of para-toluenesulfonic acid was added. The reaction was allowed to run for 12 hours on reflux in the dark. Dichloromethane (200 mL) and water (500 mL) were then added. The aqueous phase was extracted after washing with 3×100 mL of dichloromethane. The combined organic phases were extracted after washing with 3×100 mL of saturated sodium bicarbonate solution and 3×100 mL of saturated sodium chloride solution. The organic phase was then dried with magnesium sulfate and evaporated. 3.2 grams (56% yield) of a pale, yellow oil were obtained.

Compound E is the diphenyl carbonate of ninhydrin bisphenol, and was formed using a similar procedure to that described in Example 1. Compound E is illustrated below:

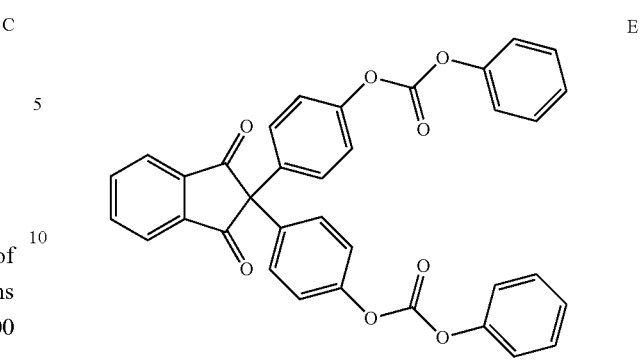

E

To form compound E, a bisphenolic starting material was first formed from ninhydrin. For this first step, 18 grams (101 mmol) of ninhydrin were dissolved in 100 mL of glacial acetic acid. 19 grams (2 equivalents) of phenol and 10 mL of 98% sulfuric acid were added slowly to the solution. During addition, the temperature was maintained between 0° C. and room temperature. The system temperature was then brought to 90° C. for four hours. Then, 200 mL of water and 300 mL of chloroform were added. The mixture was washed with 4×500 mL of 5% bicarbonate solution (until no more carbon dioxide was expelled) and then the organic phase was filtered after drying with magnesium sulfate. After evaporation, yellow crystals of the product were obtained at 85% yield. This product decomposed before melting.

For the second reaction step in forming compound E, the diphenyl carbonate derivative of the ninhydrin bisphenol, 3.9 grams of ninhydrin bisphenol (14.7 mmol) were dissolved in dichloromethane (100 mL). 3.6 mL of TEA (25.5 mmol, 2.2 equivalents) and 3.1 mL of phenyl chloroformate (24.5 mmol, 2.1 equivalents) were then added to the solution. The phenyl chloroformate was added dropwise to prevent overheating. The mixture was allowed to react for three hours. The mixture was then washed with 3×100 mL of 5% citric acid and 3×100 mL of sodium bicarbonate solution (5%). After further cleaning with saturated sodium chloride solution (2×100 mL), extraction, and crystallization at room temperature (12 hours), pale yellow crystals of the final product was obtained. This product had a melting point of 162.3° C.

UV Results for Reaction Process 2 and Maleimidophenol Crosslinking Candidates

These five compounds, A, B, C, D, and E, were then tested. First, calibration parameters were determined as above in Example 1. The calibration parameters for A, B, C, D, and E are shown below in Table 4.

TABLE 4

| Compound | Calibration curve | $\lambda$ (nm) | Range (mM) |
|---|---|---|---|
| A | A = 1398364.57 · [C] + 64456.21 | 264 | 0.17-5.18 |
| B | A = 1597511.76 · [C] + 127521.3 | 264 | 0.15-4.43 |
| C | A = 44502 · [C] + 5516.5 | 264 | 0.10-4.73 |
| D | A = 37952 · [C] + 6120.8 | 282 | 0.18-4.27 |
| E | A = 428208 · [C] + 24451 | 264 | 0.08-3.85 |

A is the absorbance, and [C] is the concentration of the compound in mM.

Next, a solution of each compound was made in dichloromethane, with about 60 mM concentration of the compound. Each compound was added to a quartz cuvette filled with 800 microliters (μL) of dichloromethane, and 200 μL of either ethanol or methanol. The solution was irradiated under UV light generated by a mercury arc lamp (AceGlass Lamp, 450 W). The irradiation lasted between 2 minutes and 30 minutes. Before and after irradiation, a 50 μL sample from the cuvette was added to 1000 microliters (μL) of MeOH and analyzed by UPLC to follow the disappearance of starting material. The results are shown in Table 5.

TABLE 5

| Compound | Methanol 20% | Ethanol 20% | Did gel form in solution? | Was gel content measured? |
|---|---|---|---|---|
| A | k = 0.022 min$^{-1}$ | k = 0.12 min$^{-1}$ | Y | N |
| B | k = 0.03 min$^{-1}$ | k = 0.04 min$^{-1}$ | Y | N |
| C | k = 0.020 min$^{-1}$ | k = 0.025 min$^{-1}$ | N | N |
| D | k = 0.022 min$^{-1}$ | k = 0.18 min$^{-1}$ | Y | N |
| E | k~0 min$^{-1}$ | k~0.0 min$^{-1}$ | — | — |

Comparing Compound A to the benzophenone in Table 2, the difference is in the group attached to the benzophenone (phenyl carbonate versus ethyl acetate). Compound A has a slower decomposition rate (0.12 vs. 0.22), possibly because of the lower steric hindrance of the ethyl group compared with a phenyl group of the phenyl carbonate moiety.

Looking at Compound B, the possible effect of the steric hindrance is apparently greater on the kinetics of the reaction. The kinetics are 3 times slower than Compound A. Two lateral chains contribute more to the slowing down of the reaction.

The 4,4'-bis(diphenyl carbonate)benzophenone compound was also synthesized. However, this compound had solubility problems in all tested solvents.

The following conclusions could be drawn. First, steric hindrance may contribute to slowing down the photochemical reactions (i.e. dimerization of the radical). Second, the endcap acetoxy functionality (i.e. Compound A) should be able to crosslink in polycarbonates to the same extent as 4-hydroxybenzophenone. Third, endcap molecules with a chain spacer equal or larger than an acetoxy group seem to decompose at a minimum rate of 0.12 min$^{-1}$ in 20% EtOH or 0.022 min$^{-1}$ in 20% MeOH can be considered candidates for crosslinker endcaps (under the AceGlass UV lamp irradiation conditions). Fourth, co-monomer molecules with two acetoxy sidechains (or larger) decompose at a very slow rate of 0.04 min$^{-1}$ in 20% EtOH or 0.03 in 20% MeOH and are likely not good crosslinking candidates.

Polycarbonate Crosslinking Evaluations

Compound A was used as an end-cap for a bisphenol-A polycarbonate. The ethyl ester derivative of 4-hydroxybenzophenone (compound A) was hydrolyzed following a procedure known in the art: 34 mmol of compound A were dissolved in 40 mL of tetrahydrofuran and 20 mL of NaOH aqueous solution at 20% w/w. The solution was refluxed at 80° C. for 3 hours. Upon complete hydrolysis, the solution was acidified to pH~1 and the precipitate was filtered and the powder washed with HCl 0.1 M, washed 3×50 mL of neutral water and dried in the oven for 6 hours (mp 155.2° C.).

The acid of compound A thus obtained was used as an end-cap for bisphenol-A polycarbonate. 35 grams (153 mmol) of bisphenol-A were suspended in 500 mL of dichloromethane and 300 mL of water. 4-(2-acetoxy)benzophenone acetic acid (Compound A, 1.57 grams, 6.1 mmol, 4% mol/mol) and triethylamine (0.43 mL, 2% mol/mol) were added into the reactor. Phosgene was bubbled through the reactor (2 g/min) for 12 minutes and the pH maintained at pH~9.5. The polymer was washed with 0.1M HCl and cleaned with 5×500 mL of water. After precipitation a polymer was obtained (Mw=19462, PDI 3.19, Tg=149.8 C). Upon irradiation of a hot pressed film (36 J/cm$^2$), the film formed a gel after dissolution in dichloromethane.

Next, Compound B was used as a comonomer for a bisphenol-A polycarbonate. The disubstituted ethyl ester derivative of 4,4'-dihydroxybenzophenone (compound B) was hydrolyzed following a procedure known in the art. 34 mmol of compound B were dissolved in 40 mL of tetrahydrofuran and 20 mL of NaOH aqueous solution at 20% w/w. The solution was refluxed at 80° C. for 3 hours. Upon complete hydrolysis, the solution was acidified to pH~1 and the precipitate was filtered and the powder washed with 0.1 M HCl, washed 3×50 mL of neutral water and dried in the oven for 6 hours (mp 241.1° C.).

The diacid of compound B thus obtained was used as a comonomer in a bisphenol-A polycarbonate copolymer. Bisphenol-A (35 grams, 153 mmol) and diacid 4,4'-bis(2-acetoxy)benzophenone (5 grams, 15 mmol, 10% mol/mol) were suspended in a solution of dichloromethane (500 mL) and water (300 mL). Transfer agent (methyl tributylammonium chloride, 1% mol/mol), triethylamine (0.43 mL, 2% mol/mol) and p-cumylphenol (1.43 grams, 7 mmol, 4% mol/mol) were added. After that, phosgene was bubbled through the solution at 1 g/min for 7 minutes at pH 6 and 18 minutes at pH 9.5. After washing with 1M HCl and cleaning with 5×600 mL of water, the polymer was precipitated (Mw=21114, PDI 4.11, Tg=142.8 C). A hot pressed film, after irradiation using UV light (36 J/cm$^2$), formed a gel.

Compound D was also used as an end-cap for a bisphenol-A polycarbonate. Bisphenol-A (35 grams, 153 mmol) and 6-maleimidohexanoic acid (1.30 grams, 6.1 mmol, 4% mol/mol) were suspended in a solution of dichloromethane (500 mL), water (300 mL) and triethylamine (0.43 mL, 6.3 mmol, 2% mol/mol). After that, phosgene was bubbled through the solution at 1 g/min for 7 minutes at pH 6 and 18 minutes at pH 9.5. After washing with 1M HCl and cleaning with 5×600 mL of water, the polymer was precipitated (Mw=25494, PDI 3.31, Tg=147.3° C.). A hot pressed film, after irradiation using UV light (36 J/cm$^2$), formed a gel.

Compound C was also used as an end-cap for bisphenol-A polycarbonates. Table 6 describes the results of irradiating compounds A, B, C, and D.

TABLE 6

| Compound | Did gel form in solution? | Was gel content measured? |
|---|---|---|
| A | Y | N |
| B | Y | N |
| C | N | N |
| D | Y | N |

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:
1. A method of identifying whether a crosslinker candidate is a suitable crosslinking agent for polycarbonates and co-polycarbonates, comprising:
synthesizing an aromatic carbonate, aromatic ester, or aliphatic ester derivative from the crosslinker candidate to form an initial product;
irradiating a solution containing a known concentration of the initial product with ultraviolet light for a first time period;
determining at least one of (i) a first-order kinetic rate constant for the disappearance of the initial product, or (ii) whether a first threshold amount of the initial product disappeared during the first time period; and
based on the value of the first-order kinetic rate constant for the disappearance of the initial product or on the actual amount of the initial product that disappears during the first time period, identifying whether the crosslinker candidate as is a suitable crosslinking agent;
wherein (i) the crosslinker candidate is a potential endcapping agent and the crosslinker candidate is identified as a suitable crosslinking agent if the first-order kinetic rate constant is determined, and the first-order kinetic rate constant is at least 0.1 min$^{-1}$ when measured in a solution of 80% dichloromethane/20% ethanol (v/v) that is irradiated with an ultraviolet light dosage of about 5 J/cm$^2$ to about 90 J/cm$^2$ of UVA radiation; or (ii) wherein the crosslinker candidate is identified as a suitable crosslinking agent if the first threshold amount of the initial product disappeared during the first time period is determined, and at least 60% of the initial product disappeared during the first time period when measured in a solution of 80% dichloromethane/20% ethanol (v/v) that is irradiated with an ultraviolet light dosage of about 5 J/cm$^2$ to about 90 J/cm$^2$ of UVA radiation.

2. The method of claim 1, wherein the first time period is about 30 minutes.

3. The method of claim 1, wherein the crosslinker candidate is a potential endcapping agent and the crosslinker candidate is identified as a suitable crosslinking agent if the first-order kinetic rate constant is at least 0.22 min$^{-1}$ when measured in a solution of 80% dichloromethane/20% ethanol (v/v).

4. The method of claim 1, further comprising periodically sampling the solution during the first time period to obtain a plurality of samples, and measuring a remaining amount of the initial product in each sample.

5. The method of claim 1, wherein the aromatic carbonate derivative of the crosslinker candidate is synthesized by reacting the crosslinker candidate with phenyl chloroformate.

6. The method of claim 1, wherein the aromatic ester or aliphatic ester derivatives of the crosslinker candidate are synthesized by reacting the crosslinker candidate with an aromatic or alkyl alcohol, respectively, and catalytic amount of acid.

7. The method of claim 1, wherein the crosslinker candidate is a diaromatic ketone or a maleimide.

8. A method of identifying a suitable crosslinking agent for polycarbonates and co-polycarbonates, comprising:
synthesizing an aromatic carbonate, aromatic ester, or aliphatic ester derivative from a crosslinker candidate to form an initial product;
irradiating a solution containing a known concentration of the initial product with ultraviolet light for a first time period;
determining a first-order kinetic rate constant for the disappearance of the initial product; and
based on the value of the first-order kinetic rate constant for the disappearance of the initial product, identifying the crosslinker candidate as a suitable crosslinking agent;
wherein the crosslinker candidate is a difunctional monomer; and the crosslinker candidate is identified as a suitable crosslinking agent if the first-order kinetic rate constant is at least 0.04 min$^{-1}$ in a solution of 80% dichloromethane/20% ethanol (v/v).

9. The method of claim 8, wherein the solution is irradiated with an ultraviolet light dosage of about 5 J/cm$^2$ to about 90 J/cm$^2$ of UVA radiation.

10. The method of claim 8, further comprising periodically sampling the solution during the first time period to obtain a plurality of samples, and measuring a remaining amount of the initial product in each sample.

11. The method of claim 8, wherein the aromatic ester or aliphatic ester derivatives of the crosslinker candidate are synthesized by reacting the crosslinker candidate with an aromatic or alkyl alcohol, respectively, and catalytic amount of acid.

12. The method of claim 8, wherein the crosslinker candidate is a diaromatic ketone of Formula (I) or a maleimide of Formula (II):

Formula (I)

where R$^1$ and R$^2$ are independently aryl, and at least one of R$^1$ and R$^2$ is substituted with a sidechain containing a reactive group:

Formula (II)

where R$^3$, R$^4$, and R$^5$ are independently hydrogen, halogen, alkyl, or aryl, and at least one of R$^3$, R$^4$, and R$^5$ is substituted with a sidechain containing a reactive group.

13. A method of identifying a suitable crosslinking agent for polycarbonates and co-polycarbonates, comprising:
synthesizing an aromatic carbonate, aromatic ester, or aliphatic ester derivative from a crosslinker candidate to form an initial product;
irradiating a solution containing a known concentration of the initial product with ultraviolet light for a first time period;
determining a first threshold amount of the initial product disappeared during the first time period; and
if at least 60% of the initial product disappeared during the first time period, then: synthesizing at least one article from a polymer that contains the crosslinker candidate as an endcapping agent or as a co-monomer;
irradiating the at least one article with a specified UV dosage;

either (i) determining an increase in crosslink density of the article after the irradiation with the specified UV dosage, or (ii) measuring a gel formation percentage of the article after the irradiation with the specified UV dosage; and based on the increase in crosslinking density, or the gel formation percentage, identifying the crosslinker candidate as a suitable crosslinking agent;

wherein the crosslinker candidate is identified as a suitable crosslinking agent if the increase in crosslink density is at least 0.0015, or if the gel formation percentage is at least 6% as measured on a 3.2 mm thick Izod bar with a weight of at least 2.9 grams.

14. The method of claim 13, further comprising periodically measuring the crosslink density of the at least one article during the irradiation with the specified UV dosage.

15. The method of claim 13, wherein the increase in crosslink density, x, is determined by the following formula:

$$Mw = \frac{Mw0}{1 - 2 \cdot n \cdot x}$$

wherein Mw0 is the weight average molecular weight of the polymer before irradiation; Mw is the weight average molecular weight of the polymer after irradiation; and n is the number of monomers for the given weight average molecular weight.

16. The method of claim 13, wherein the gel formation percentage is measured by weighing the article; dissolving the article in dichloromethane to obtain the gel; and weighing the gel to obtain the ratio of gel weight to article weight.

* * * * *